(12) United States Patent
Ryu et al.

(10) Patent No.: US 9,128,009 B2
(45) Date of Patent: Sep. 8, 2015

(54) MEASUREMENT DEVICE FOR MINIMIZING EXTERNAL MAGNETIC DISTURBANCE

(75) Inventors: Kwon Sang Ryu, Daejeon (KR); Soo Young Park, Daejeon (KR); Seung Hoon Nahm, Daejeon (KR); Young Il Kim, Daejeon (KR)

(73) Assignee: Korea Research Institute of Standards and Science, Daejeon (KR)

(*) Notice: Subject to any disclaimer, the term of this patent is extended or adjusted under 35 U.S.C. 154(b) by 701 days.

(21) Appl. No.: 13/514,881

(22) PCT Filed: Nov. 3, 2010

(86) PCT No.: PCT/KR2010/007708
§ 371 (c)(1),
(2), (4) Date: Aug. 13, 2012

(87) PCT Pub. No.: WO2011/071244
PCT Pub. Date: Jun. 16, 2011

(65) Prior Publication Data
US 2012/0310581 A1    Dec. 6, 2012

(30) Foreign Application Priority Data
Dec. 8, 2009 (KR) .................... 10-2009-0121039

(51) Int. Cl.
*G01D 18/00* (2006.01)
*G01N 3/00* (2006.01)

(52) U.S. Cl.
CPC .......... *G01N 3/00* (2013.01); *G01N 2203/0075* (2013.01); *G01N 2203/0635* (2013.01)

(58) Field of Classification Search
CPC .............. G01N 2203/0075; G01N 2203/0635; G01N 3/00; G01V 1/001
See application file for complete search history.

(56) References Cited

U.S. PATENT DOCUMENTS

| 4,165,479 A | 8/1979 | Mansfield |
| 4,442,404 A | 4/1984 | Bergmann |
| 6,404,340 B1 | 6/2002 | Paradiso et al. |
| 8,128,564 B2 * | 3/2012 | Kwon et al. ............. 600/438 |

FOREIGN PATENT DOCUMENTS

| JP | 2002-232182 A | 8/2002 |
| KR | 10-0608110 | 4/2006 |

OTHER PUBLICATIONS

International Search Report dated Jun. 29, 2011 in International Application No. PCT/KR2010/007708.

* cited by examiner

*Primary Examiner* — Elias Desta
(74) *Attorney, Agent, or Firm* — The Webb Law Firm

(57) ABSTRACT

Provided is a ΔE measuring device minimizing external magnetic disturbance, more particularly, a ΔE measuring device measuring a change (ΔE) in elastic modulus under a magnetic field by removing a bias effect by the earth's magnetic field and a magnetic tool and device and using a magneto acoustic resonance method. With the ΔE measuring device, a space minimizing external magnetic disturbance using three-axis Helmholtz coils is provided and the ΔE measuring device having a plurality of coil structures is inserted into the space, thereby making it possible to minimize external magnetic field disturbance.

8 Claims, 8 Drawing Sheets i) T>Tc ii) T<Tc

H=0 iii) T<Tc

H

MEASUREMENT DEVICE FOR MINIMIZING EXTERNAL MAGNETIC DISTURBANCE

CROSS-REFERENCE TO RELATED APPLICATIONS

This application is the United States national stage of International Application No. PCT/KR2010/007708, filed Nov. 3, 2010, and claims priority to Korean Patent Application No. 10-2009-0121039, filed Dec. 8, 2009, the disclosures of which are hereby incorporated in their entirety by reference.

BACKGROUND OF THE INVENTION

1. Field of the Invention

TECHNICAL FIELD

The present invention relates to a ΔE measuring device minimizing external magnetic disturbance, and more particularly, to a ΔE measuring apparatus measuring a change (ΔE) in elastic modulus under a magnetic field by removing a bias effect by the earth's magnetic field and a magnetic tool and device and using a magneto acoustic resonance method.

2. Description of Related Art

Generally, in order to form a space not having a magnetic field by reducing a change amount in the earth's magnetic field, a method (hereinafter, referred to as a magnetic shielding method) of shielding a magnetic field using a magnetic material having high magnetic permeability, a method of measuring a change amount in external magnetic field and applying magnetic fields having the same magnitude as each other and the opposite directions to each other to offset a magnetic field (hereinafter, a magnetic field offsetting method), and the like, have been suggested.

An example of the latter may include an apparatus as shown in FIG. 1. FIG. 1 shows a structure of a direct current magnetic field offsetting part in the earth's magnetic field offsetting apparatus. Magnetic fields having the same magnitude as and the opposite direction to the earth's magnetic field are generated in Helmholtz coils in each direction using a direct current (DC) current source to form a space in which a DC earth magnetic field component is offset.

To this end, each of large three-axis Helmholtz coil apparatuses 102, 104, and 106 is adjusted and installed in a non-magnetic building 10 in a vertical direction, a north-south direction, and an east-west direction, and small Helmholtz coils 122, 124, and 126 are adjusted to coincide with each other in each direction and are connected in series with each other in an observing chamber 12 positioned at a point spaced apart from the building to the south by 50 m. Three current sources 142, 144, and 146 for offsetting a DC earth's magnetic field are installed in a measuring chamber 15 spaced apart from the non-magnetic building 10 to the north by 50 m.

In addition, in order to allow coil constants of two Helmholtz coils offsetting a vertical component to coincide with each other, a branch resistor (RV), a branch resistor (RN) connected in a north-south (N-S) direction, and a branch resistor (RE) connected in an east-west (E-W) direction are used. In addition, since the east-west direction is the same direction as that of a solenoid that is a precise magnetic field generator, branch resistors RE1 and RE2 are used in order to improve uniformity in a central space of the Helmholtz coils and allow coil constants of two large Helmholtz coils to coincide with each other.

In the case of each of the Helmholtz coils, a DC coil and a coil offsetting a variance according to a time are wound around the same coil bobbin in order to simultaneously offset a DC component and a component according to a time.

Two Helmholtz coils should be installed in a state in which they are spaced apart from each other by 30 m or more in order to exclude mutual interference. The two Helmholtz coils have different sizes, but have the same coil constant (a size of a magnetic field according to current) and are connected in series with each other to simultaneously offset the earth's magnetic fields at two places.

Next, in order to remove a component changed according to a time, a magnetic resonance frequency that is in proportion to a change amount in earth's magnetic field is measured using a magnetic resonance measurer and is compared with a first set reference frequency to generate current (voltage) corresponding to a difference between the above-mentioned two frequencies (a difference between magnetic fields) using a phase comparator, and the current (voltage) is applied to the Helmholtz coils to generate magnetic fields that is in proportion to a magnitude of the earth's magnetic field in an opposite direction to that of the earth's magnetic field, thereby offsetting the earth's magnetic field.

Since the apparatus shown in FIG. 1 is described in detail in Korean Patent Registration No. 10-0608110 (Title: Apparatus for Offsetting Earth's Magnetic Field), an additional description will be omitted.

However, according to the related art, in order not to have any external effect on the non-magnetic building, the non-magnetic building should be built without using a magnetic material such as iron.

In addition, there is a spatial limitation in that the non-magnetic building should be spaced apart from a road by a predetermined distance or more in order to remove interference from the outside.

Therefore, disturbance is easily generated due to a surrounding environment (for example, home appliances, a steel-frame building, or the like) having magnetism as well as an external magnetic field at a place except for the non-magnetic building.

Further, since a soft magnetic material is easily affected by the appliances, the steel-frame structure, or the like, having magnetism in the vicinity thereof, it is difficult to perform precise measurement.

SUMMARY OF THE INVENTION

Technical Problem

An object of the present invention is to provide an apparatus capable of removing a bias effect due to the earth's magnetic field and minimizing external magnetic disturbance due to magnetism of home appliances and a steel-frame structure.

Another object of the present invention is to provide an apparatus capable of precisely measuring a change amount in elastic modulus under a magnetic field of a magnetic material (particularly, a soft magnetic material) by minimizing external magnetic disturbance.

Technical Solution

In one general aspect, a ΔE measuring device minimizing external magnetic disturbance includes: three-axis Helmholtz coils arranged in x, y, and z axis directions to remove the earth's magnetic field; a three-axis magnetic sensor installed at one side of the three-axis Helmholtz coils to measure magnetic fields formed in the three-axis Helmholtz coils; a second power supply unit supplying offset current offsetting the measured magnetic fields to the three-axis Helmholtz coils according to the measured magnetic fields; a tertiary coil inserted into and seated in the three-axis Helmholtz coils; a secondary coil inserted into and seated in the tertiary coil; a primary coil inserted into and seated in the secondary coil and having a sample inserted thereinto and seated therein, the sample corresponding to an object to be measured; a signal generator applying an AC current signal to the secondary coil; a first power supply unit applying a DC current signal to the tertiary coil; a signal measuring unit measuring a magneto acoustic resonance frequency detected in the primary coil; and a calculating unit calculating an elastic modulus using the magneto acoustic resonance frequency and commanding the second power supply unit to supply the offset current.

Here, when the AC current signal is applied to the secondary coil using the signal generator and an output signal of the primary coil measuring the magneto acoustic resonance signal is measured using the signal of the signal generator as a reference signal while a frequency of the signal is increased, the magneto acoustic resonance signal as shown in FIG. 7 is measured, thereby making it possible to calculate the elastic modulus.

The elastic modulus may be calculated by the following Equation:

$$E = 4l^2 f_r^2 \rho$$

(where E indicates an elastic modulus depending on the magneto acoustic resonance frequency ($f_r$), l indicates a length of the sample, $f_r$ indicates the magneto acoustic resonance frequency, and $\rho$ indicates density).

The first power supply unit may stepwise increase the current applied to the tertiary coil to change a magnetic field applied to the sample, and the second power supply unit may supply both of the DC and AC current signals The calculating unit may include an analog to digital converting unit transmitting a signal to and receiving the signal from at least any one of the three-axis magnetic sensor, the first power supply unit, the second power supply unit, the signal generator, and the signal measuring unit.

Coils of each axis of the three-axis Helmholtz coils may be configured of two coaxial coils which are positioned to be spaced apart from each other by a radius thereof.

Advantageous Effects

According to the exemplary embodiment of the present invention, a space minimizing external magnetic disturbance using the three-axis Helmholtz coils, the elastic modulus is measured in a magneto-acoustic resonance scheme, and an elastic modulus and ΔE measuring device having a plurality of coil structures capable of measuring a change in elastic modulus under a magnetic field is inserted into the space, thereby making it possible to minimize external magnetic field disturbance.

BRIEF DESCRIPTION OF THE DRAWINGS

The above and other objects, features and advantages of the present invention will become apparent from the following description of preferred embodiments given in conjunction with the accompanying drawings, in which.

DETAILED DESCRIPTION OF THE INVENTION

Hereinafter, preferred embodiments of the present invention will be described in detail with reference to the accompanying drawings.

In Korea, a magnitude of the earth's magnetic field on the earth's surface is about 0.5 G (Gauss). A magnetic material (for example, an amorphous material) having low coercive force and high magnetic permeability is significantly magnetized even with this earth's magnetic field. In addition, a magnetic material (particularly, a soft magnetic material) is affected even by an external environment having magnetism.

Figure 5:
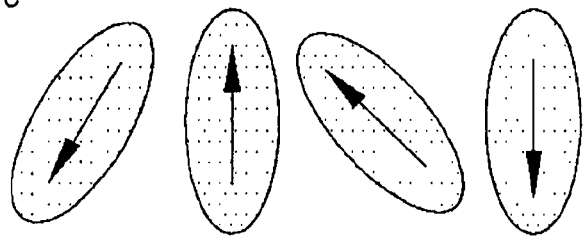
FIG. 5 is a state diagram showing a state in which a size of a magnetic material is changed in when the magnetic material is exposed to a magnetic field.
Figure 5:
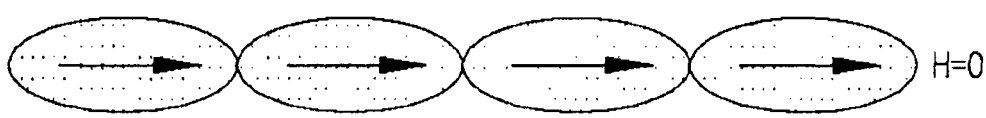
Figure 5:
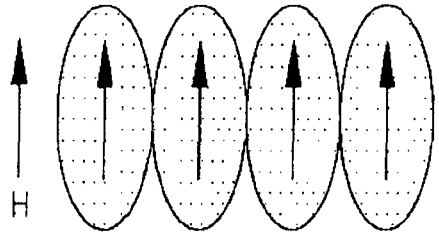

FIG. 5 shows an example of magnetic strain.

1) of FIG. 5 shows that a magnetic domain is arranged in a random direction in the case in which a temperature is higher than the Curie temperature (T>Tc).

2) of FIG. 5 shows that a magnetic domain is ideally arranged by spontaneous magnetization of the magnetic material in the case in which a temperature of a magnetic material is lower than the Curie temperature (Tc) and a magnetic field is not present outside.

3) of FIG. 5 shows that a magnetic domain is arranged toward an applied external magnetic field to generate magnetic strain (ΔL2) in the case in which a temperature of a magnetic material is lower than the Curie temperature (Tc) and the magnetic field is applied from the outside in a direction vertical to a direction in which the magnetic material is spontaneously magnetized. This means that strain is generated even though physical stress is not applied from the outside to the magnetic material.

Figure 6:
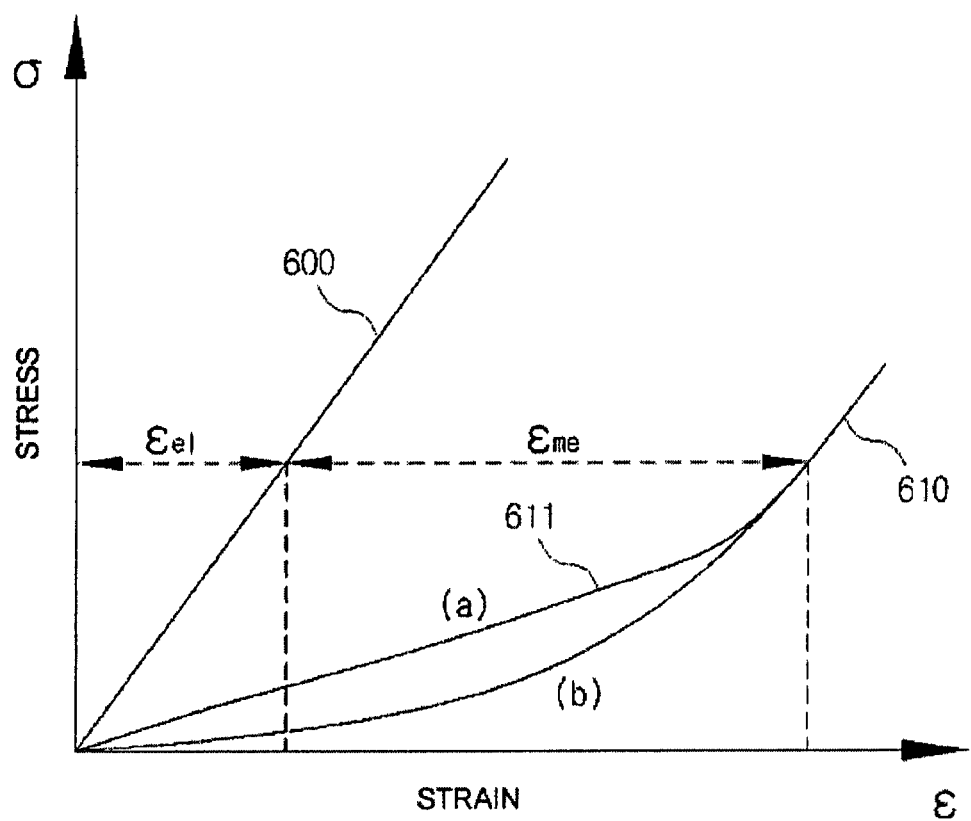
FIG. 6 is a graph comparing stress-strain rate curves of a magnetic material and a non-magnetic material with each other.

FIG. 6 is a graph comparing stress-strain rate curves of a magnetic material and a non-magnetic material with each other under a magnetic field.

In FIG. 6, a curve 600 for a non-magnetic material or a magnetically saturated magnetic material and a curve 611 for a demagnetized magnetic material are shown. It may be appreciated that larger strain is generated in the demagnetized magnetic material than in the non-magnetic material or the saturated magnetic material under the same stress. The reason is that magnetic strain is added in the case of the magnetic material as described above. The curves 610 and 611 for magnetic materials may be divided as follows.

(a) magnetic material 611 having strong anisotropy (b) magnetic material 610 having weak anisotropy That is, a gradient (a)>(b). The reason is that stronger anisotropy acts on the magnetic material having the strong anisotropy.

When an elastic modulus (E) and a change (ΔE) in elastic modulus are calculated based on the graph shown in FIG. 6, they may be presented by the following Equation 1.

$$E_d = \frac{\sigma}{\varepsilon_{el} + \varepsilon_{me}} \qquad \text{[Equation 1]}$$

Where $E_d$ indicates an elastic modulus in a demagnetized state, $\varepsilon_{el}$ indicates elastic strain generated in any material regardless of magnetism, $\varepsilon_{me}$ indicates magnetic elastic strain corresponding to a value due to rearrangement of a magnetic domain vector by applied stress, and $\sigma$ indicate stress.

$$E_s = \frac{\sigma}{\varepsilon_{el}} \qquad \text{[Equation 2]}$$

Where $E_s$ indicates an elastic modulus in a saturated state or an elastic modulus in a non-magnetic material.

The following Equation 3 is derived from Equation 1 and Equation 2.

$$\frac{\Delta E}{E_{\mathit{eff}}} = \frac{E_s - E_d}{E_d} = \frac{\varepsilon_{me}}{\varepsilon_{el}} \qquad \text{[Equation 3]}$$

As an example of a value of $\Delta E/E_{\mathit{eff}}$, nickel (Ni) has a value of $\Delta E/E_{\mathit{eff}}$ of about 6% and iron has a value of $\Delta E/E_{\mathit{eff}}$ smaller than 1%.

Therefore, referring to FIG. 6 and Equations 1 to 3, $\Delta E$ corresponds to a difference between initial gradients in the stress-strain curves of the demagnetized magnetic material and the saturated magnetic material.

As described above, in order to perform precise measurement of the magnetic material, a $\Delta E$ effect should be measured in a state in which the earth's magnetic field and the external magnetic field are removed.

Figure 1:
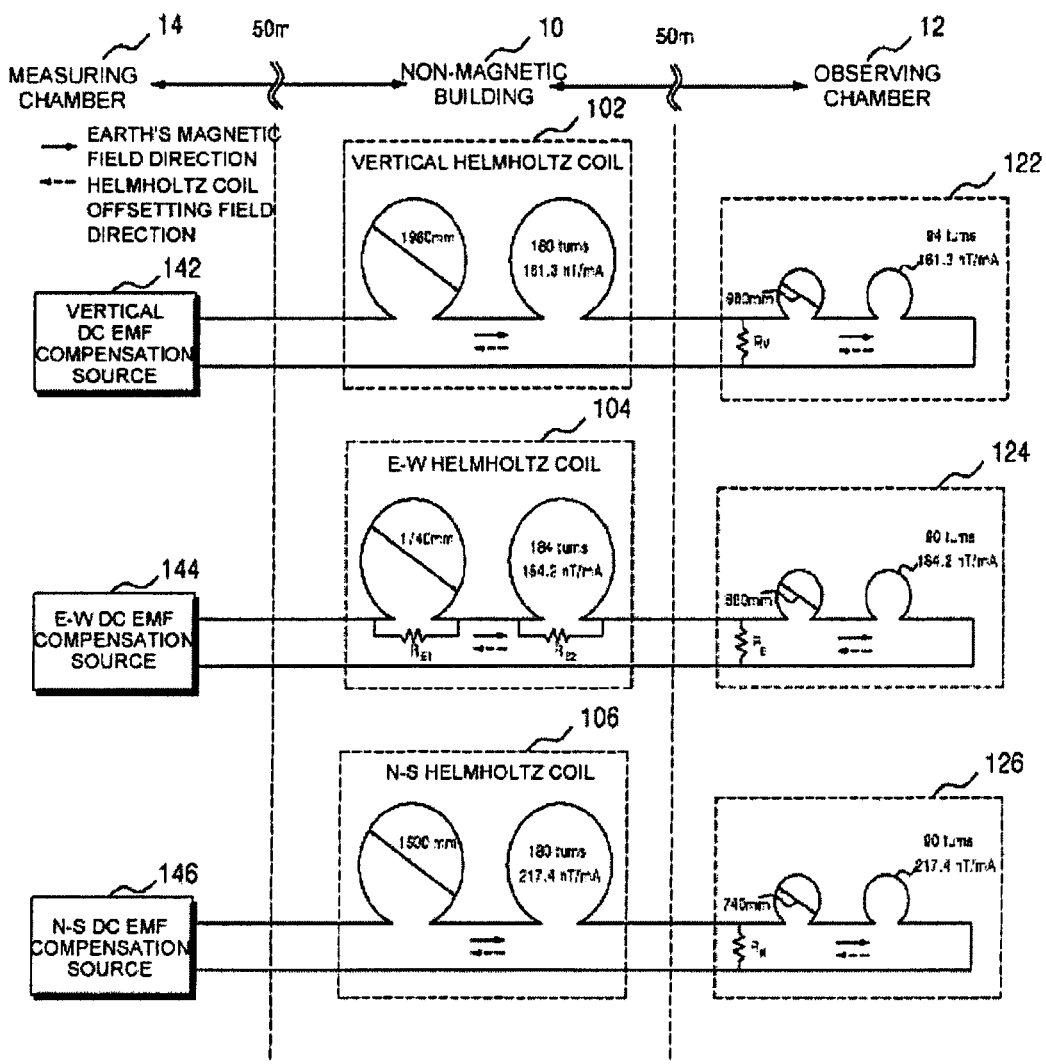
FIG. 1 is a configuration diagram of an earth's magnetic field offsetting apparatus according to the related art.
Figure 2:
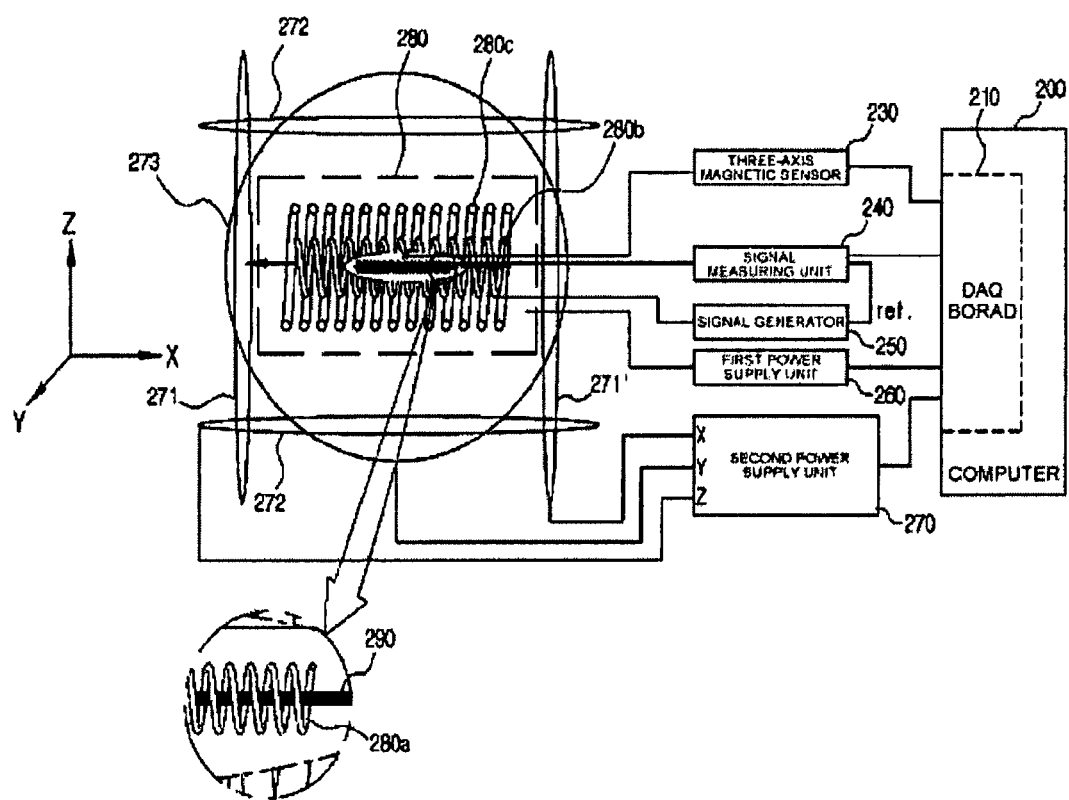
FIG. 2 is a configuration diagram of a ΔE effect measuring device according to an exemplary embodiment of the present invention.

A configuration of a $\Delta E$ effect measuring device is shown in FIG. 2.

That is, FIG. 2 is a configuration diagram of the $\Delta E$ effect measuring device according to an exemplary embodiment of the present invention. Referring to FIG. 2, the $\Delta E$ effect measuring device is configured to include three-axis Helmholtz coils 271, 272, and 273, a $\Delta E$ measuring coil 280 inserted into these three-axis Helmholtz coils 271, 272, and 273, a three-axis magnetic sensor 230 measuring a signal output from a three-axis magnetic sensor in the three-axis Helmholtz coils 271, 272, and 273, a signal measuring unit 240 measuring a signal from a sample 290 which is a measuring material inserted into the $\Delta E$ measuring coil, a signal generator 250 providing a signal to the $\Delta E$ measuring coil, a first power supply unit 260, a second power supply unit 270 providing a signal to the three-axis Helmholtz coils, a computer 200 having a multi-functional data Acquisition (DAQ) board 210 embedded therein in order to receive signals output from the measuring units and transfer the signals to the supply units, and the like. These components will be described below.

Figure 4:
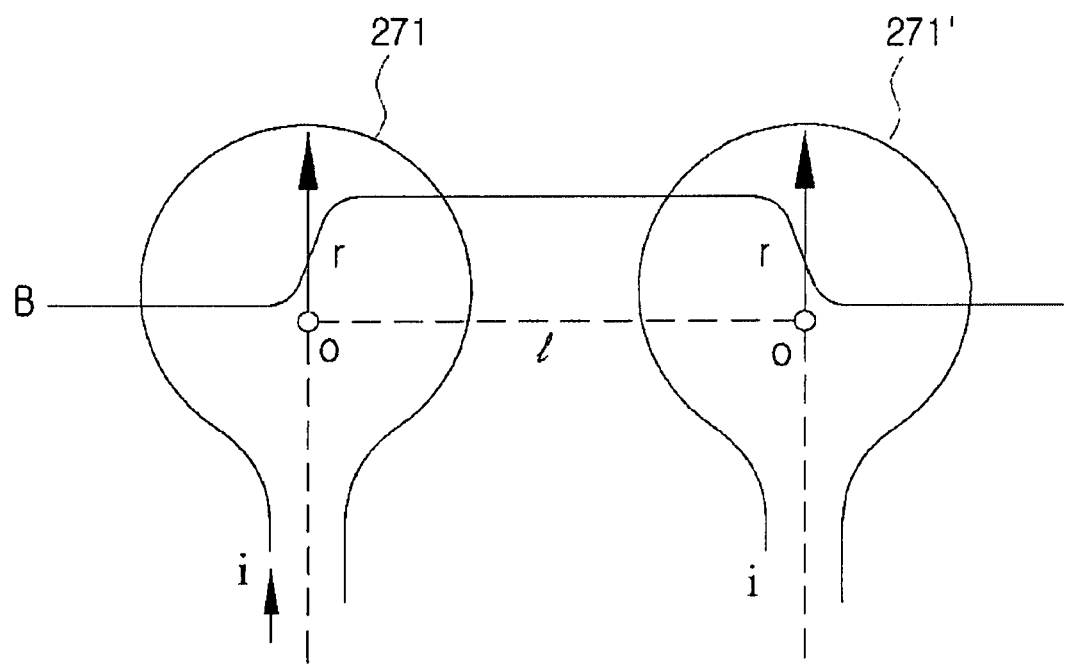
FIG. 4 is a graph showing that a magnetic field in a Helmholtz coil in the ΔE effect measuring device of FIG. 2 is substantially constantly maintained.

The three-axis Helmholtz coils 271, 272, and 273 includes x-axis coils 271 and 271', y-axis coils 273 and 273', z-axis coils 272 and 272', and the like. Here, the y-axis coil 273' is not shown. In the case of the Helmholtz coils, two coaxial coils are positioned so as to be spaced apart from each other by a diameter thereof to make a magnetic field therebetween substantially constant, which is shown in FIG. 4.

Further, in order to measure a magnetic field in the three-axis Helmholtz coils 271, 272, and 273, the three-axial magnetic sensor 230 is provided at the center of the three-axis Helmholtz coils 271, 272, and 273. The three-axis magnetic sensor 230 serves to measure the magnetic field in the three-axis Helmholtz coils 271, 272, and 273. This three-axis magnetic sensor 230 measures strength of the magnetic field to transmit the measured strength to the computer 200 through the multi-functional DAQ board 210.

Therefore, after the strength of the magnetic field at the center of the Helmholtz coil is measured using the three-axis magnetic sensor 230, a signal is transmitted from the multi-functional DAQ board 210 to the second power supply unit 270 so that a magnetic field having the same magnitude as that of the magnetic field at the center of the Helmholtz coil and the opposite direction to that of the magnetic field at the center of the Helmholtz coil is generated, and the second power supply unit converts the signal into current to apply the current to the three axis Helmholtz coils, such that external magnetic disturbance is offset, whereby a magnetic field value becomes "0". In order to facilitate the understanding, only the x-axis coil will be described by way of example.

① A magnetic field in the x-axis coils 271 and 271' is first measured.

② In the case in which the measured magnetic field is not "0", the second power supply unit 270 applies current to the x-axis coils 271 and 271'. In this case, a direction and strength of the current are adjusted so that the current has the same magnitude as and the opposite direction to the magnetic field measured in ①. These adjustment values are calculated by the computer 200 and transmitted to the second power supply unit 270 through the multi-functional DAQ board 210, and the second power supply unit 270 converts the adjustment values into the current to allow the current to the x-axis coils 271 and 271'.

③ A magnetic field in the x-axis coils 271 and 271' is again measured.

④ When the measured magnetic field becomes "0", it means that the external magnetic disturbance is offset.

When processes of ① to ④ are similarly applied to remaining y-axis and z-axis coils 272 and 273, the three-axis space magnetic disturbance is offset.

Continuously describing FIG. 2, the $\Delta E$ measurement coil 280 is inserted into and seated in the three-axis Helmholtz coils 271, 272, and 273. The $\Delta E$ measurement coil 280 includes three coils 280a, 280b, and 280c, that is, a magneto acoustic resonance signal detecting coil 280a, a frequency variable alternate current (AC) magnetic field applying coil 280b, and a variable direct current magnetic field applying coil 280c.

The sample 290 which is an object to be measured is inserted into the magneto acoustic resonance signal detecting coil 280a of the $\Delta E$ measurement coil 280. The sample 290, which is a magnetic material, may be a wire, a thick film, or the like.

The first power supply unit 260 applies DC current to the variable direct current magnetic field applying coil 280c.

The signal generator 250 serves to apply an AC current signal to the frequency variable alternate current magnetic field applying coil 280b. That is, the signal generator 250 may generate a sine wave signal having a frequency from 50 Hz to 3 MHz. Further, in the present invention, since only a small magnetic field is generated, a power amplifier is not used.

The signal measuring unit 240 serves to measure a magneto acoustic resonance signal detected in the magneto acoustic resonance signal detecting coil 280a. The signal measuring unit 240, which is a lock-in amplifier, compares frequencies of the signal generated in the magneto acoustic resonance signal detecting coil 280a and a reference signal (ref) with each other to remove noise and measure only a desired signal.

Figure 3:
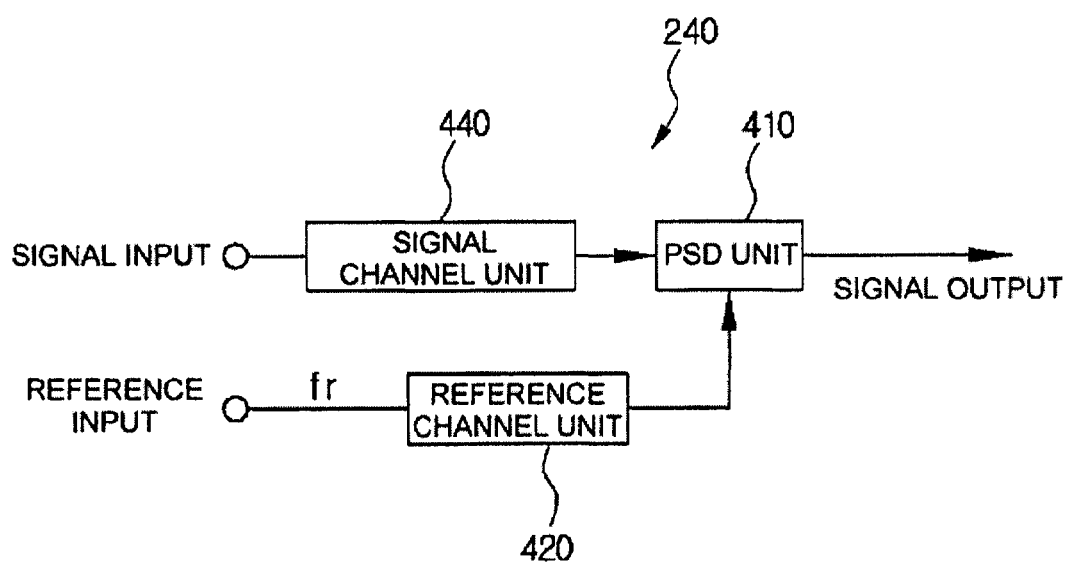
FIG. 3 is a configuration diagram of a signal measuring unit shown in FIG. 2.

A configuration diagram of the signal measuring unit 240 is shown in FIG. 3. A description thereof will be provided below in order to allow the present invention to be obviously understood.

Figure 7:
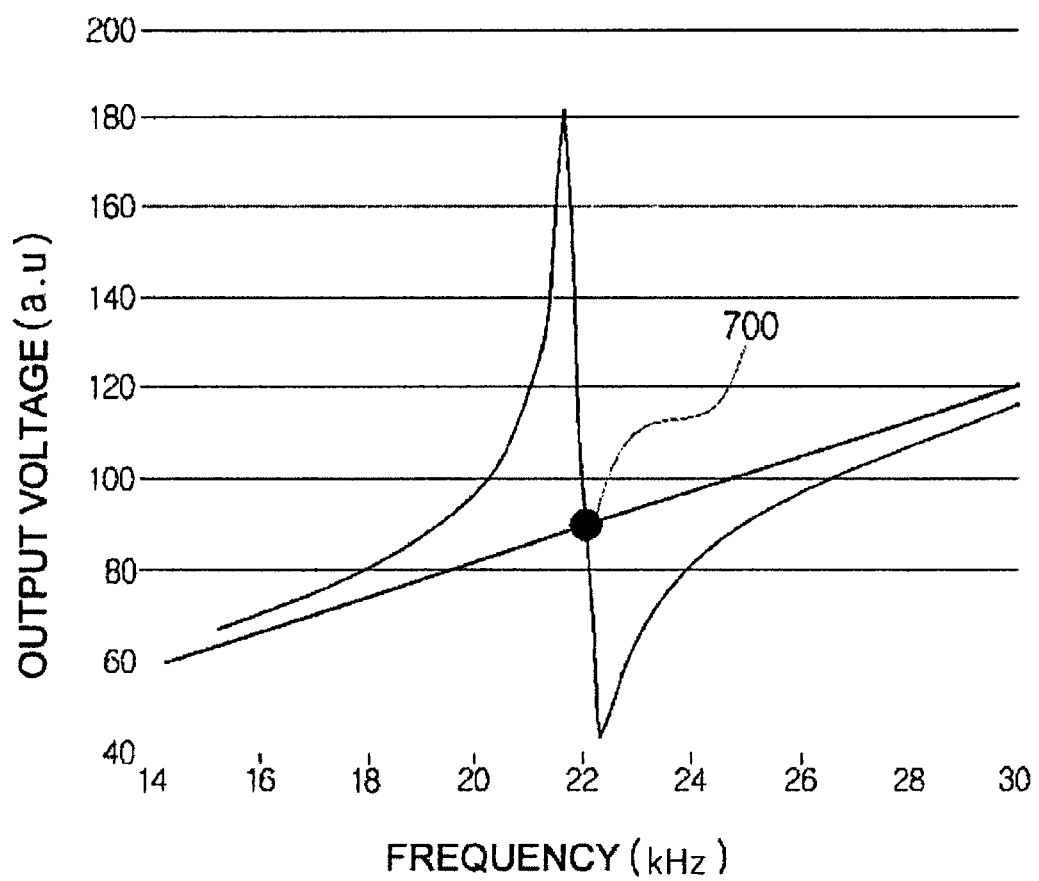
FIG. 7 is a graph of a magneto acoustic resonance frequency generated using a magneto acoustic effect according to an exemplary embodiment of the present invention.

Since the frequency variable alternate current magnetic field applying coil 280b is connected to the signal generator 250 to receive the AC signal, an AC magnetic field is generated in the magneto acoustic resonance signal detecting coil 280a. Therefore, a length of the sample 290 is also repeatedly increased and decreased finely by a magneto elastic effect and resonates at a specific frequency. This resonance is measured as a magneto acoustic resonance signal in the magneto acoustic resonance signal detecting coil 280a, which is shown in FIG. 7.

The magneto acoustic resonance frequency 700 and the signal measured in the magneto acoustic resonance signal detecting coil 280a are adjusted as a signal capable of being received in the multi-functional DAQ board 210 using the signal measuring unit 240 and then transmitted to the multi-functional DAQ board 210, and the multi-functional DAQ board 210 digitally processes the received signal to transmit the processed signal to the computer 200.

Here, an elastic modulus may be calculated using the magneto acoustic resonance frequency 700, which may be represented by the following Equation 4.

$$E = 4l^2 f_r^2 \rho \quad \text{[Equation 4]}$$

Where E indicates an elastic modulus depending on a magneto acoustic resonance frequency ($f_r$), l indicates a length of a sample, $f_r$ indicates the magneto acoustic resonance frequency, and $\rho$ indicates density.

In the case in which the elastic modulus is calculated, ΔE may be measured. ΔE may be measured by adjusting the DC current signal applied to the variable direct current magnetic field applying coil 280c, as described above. More specifically, in FIG. 3, when the first power supply unit 260 stepwise increases the DC signal applied to the variable direct current magnetic field applying coil 280c, magnetic strain is generated, such that a strain rate increases. As a result, the magneto acoustic resonance frequency measured in the magneto acoustic resonance signal detecting coil 280a is changed, and the elastic modulus calculated by Equation 4 is also changed. Therefore, a difference between an elastic modulus (E) first calculated by Equation 4 and a current elastic modulus (E) is calculated to calculate ΔE.

Figure 8:
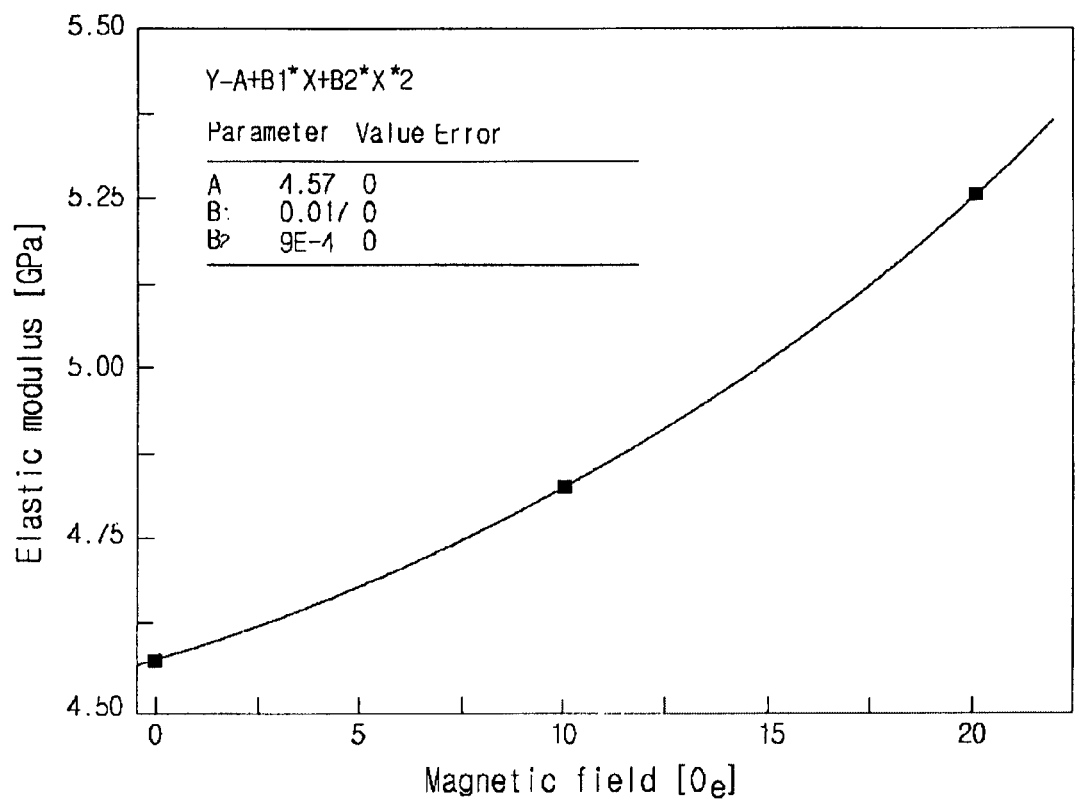
FIG. 8 is a graph showing a change in elastic modulus according to a change in magnetic field according to the exemplary embodiment of the present invention.

That is, when the magnetic field is changed, the elastic modulus is also changed, which may be represented as a graph by FIG. 8.

Here, in the graph shown in FIG. 8, a unit of the elastic modulus (E) is giga-Pascal (GPa) or $kg/mm^2$. 1 Pa=9.87*e−6 atm=1.02*e−5 $kgf/cm^2$. A unit of the magnetic field is Oe. 1 Oe=79.58 A/m.

Next, the signal measuring unit 240 shown in FIG. 3 will be described. The signal measuring unit 240 includes a signal channel unit 400, a phase sensitive detector (PSD) unit 410, and a reference channel unit 420. The signal channel unit 400 filters the magneto acoustic resonance frequency signal which is a signal input from the resonance signal detecting coil 280a to remove the noise. The reference channel unit 420 includes a phase locked loop and a phase shifter to change an input reference signal (ref).

The PSD unit 410 generates an output signal by a phase difference between the magneto acoustic resonance frequency signal and a phase shifted reference signal to transmit the output signal to the computer 200 through the multi-functional DAQ board 210 (See FIG. 2).

Although the exemplary embodiment of the present invention has been described above with reference to the accompanying drawings, it may be appreciated by those skilled in the art that the scope of the present invention is not limited to the above-mentioned exemplary embodiment, but may be variously modified. Therefore, the scope of the present invention is to be defined by the accompanying claims and their equivalents.

The invention claimed is:

1. A change in elastic modulus (ΔE) measuring device minimizing external magnetic disturbance, comprising:
   three-axis Helmholtz coils arranged in x, y, and z axis directions to remove the earth's magnetic field;
   a three-axis magnetic sensor installed at the center of the three-axis Helmholtz coils to measure magnetic fields formed in the three-axis Helmholtz coils;
   a second power supply unit supplying offset current offsetting the measured magnetic fields to the three-axis Helmholtz coils according to the measured magnetic fields;
   a variable direct current (DC) magnetic field applying coil inserted into and seated in the three-axis Helmholtz coils;
   a frequency variable alternate current (AC) magnetic field applying coil inserted into and seated in the variable DC magnetic field applying coil;
   a magneto acoustic resonance signal detecting coil inserted into and seated in the frequency variable AC magnetic field applying coil and having a sample inserted thereinto and seated therein, the sample corresponding to an object to be measured;
   a signal generator applying an AC current signal to the frequency variable AC magnetic field applying coil;
   a first power supply unit applying a DC current signal to the variable DC magnetic field applying coil;
   a signal measuring unit measuring a magneto acoustic resonance frequency detected in the magneto acoustic resonance signal detecting coil; and
   a calculating unit calculating an elastic modulus using the magneto acoustic resonance frequency and commanding the second power supply unit to supply the offset current.

2. The ΔE measuring device of claim 1, wherein the first power supply unit stepwise increases the DC current applied to the variable DC magnetic field applying coil to change a magnetic field applied to the sample, and the second power supply unit supplies both of the DC and AC current signals.

3. The ΔE measuring device of claim 1, wherein the elastic modulus is calculated by the following Equation:
   $E = 4l^2 f_r^2 \rho$ (where E indicates an elastic modulus depending on the magneto acoustic resonance frequency ($f_r$), l indicates a length of the sample, $f_r$ indicates the magneto acoustic resonance frequency, and $\rho$ indicates density).

4. The ΔE measuring device of claim 2, wherein the elastic modulus is calculated by the following Equation:
   $E = 4l^2 f_r^2 \rho$ (where E indicates an elastic modulus depending on the magneto acoustic resonance frequency ($f_r$), l indicates a length of the sample, $f_r$ indicates the magneto acoustic resonance frequency, and $\rho$ indicates density).

5. The ΔE measuring device of claim 1, wherein the calculating unit includes an analog to digital converting unit transmitting a signal to and receiving the signal from at least any one of the three-axis magnetic sensor, the first power supply unit, the second power supply unit, the signal generator, and the signal measuring unit.

6. The ΔE measuring device of claim 2, wherein the calculating unit includes an analog to digital converting unit transmitting a signal to and receiving the signal from at least any one of the three-axis magnetic sensor, the first power supply unit, the second power supply unit, the signal generator, and the signal measuring unit.

7. The ΔE measuring device of claim 1, wherein coils of each axis of the three-axis Helmholtz coils are configured of two coaxial coils which are positioned to be spaced apart from each other by a radius thereof.

8. The ΔE measuring device of claim 2, wherein coils of each axis of the three-axis Helmholtz coils are configured of two coaxial coils which are positioned to be spaced apart from each other by a radius thereof.

\* \* \* \* \*